(12) United States Patent
Gross et al.

(10) Patent No.: US 7,981,166 B2
(45) Date of Patent: Jul. 19, 2011

(54) BLEACHING AGENT HAVING CATIONIC ACYL PYRIDINIUM DERIVATIVES, CO-BLEACHING ACTIVATORS AND HYDROGEN PEROXIDE

(75) Inventors: Wibke Gross, Hueckelhoven (DE); Denise Fuhr, Duesseldorf (DE); Ralph Nemitz, Juechen (DE); Kristin Mielich, Wuppertal (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 12/940,088

(22) Filed: Nov. 5, 2010

(65) Prior Publication Data

US 2011/0047712 A1    Mar. 3, 2011

Related U.S. Application Data

(63) Continuation of application No. PCT/EP2009/051835, filed on Feb. 17, 2009.

(30) Foreign Application Priority Data

May 7, 2008    (DE) .......................... 10 2008 022 710

(51) Int. Cl.
*D06L 3/00* (2006.01)
(52) U.S. Cl. .................. 8/101; 8/107; 8/109; 8/111
(58) Field of Classification Search .............. 8/101, 107, 8/109, 111
See application file for complete search history.

(56) References Cited

U.S. PATENT DOCUMENTS 6,371,993 B1 * 4/2002 Moeller et al. .................... 8/407
2005/0262647 A1   12/2005 Hoeffkes et al.

FOREIGN PATENT DOCUMENTS

| AU | 730455 | B2 | 5/2000 |
| DE | 10148845 | A1 | 4/2003 |
| EP | 1219285 | A2 | 7/2002 |
| EP | 1882495 | A2 | 1/2008 |
| EP | 1891927 | A2 | 2/2008 |
| EP | 1905418 | A2 | 4/2008 |
| GB | 645263 | A | 10/1950 |

OTHER PUBLICATIONS

STIC Search Report dated Feb. 23, 2011.*
Schrader, Karlheinz. Grundlagen und Rezepturen der Kosmetika (Fundamentals and Formulations of Cosmetics), 2, Hüthig Buch Verlag GmbH, Heidelberg 1989.
Umbach, W. Kosmetik: Entwicklung, Herstellung und Anwendung kosmetischer Mittel, Georg Thieme Verlag, 1995.
Römp-Lexikon. Chemie. George Thieme Verlag, vol. 10, 1997, p. 1764.

* cited by examiner

Primary Examiner — Eisa B Elhilo
(74) Attorney, Agent, or Firm — David P. LeCroy

(57) ABSTRACT

Agent for bleaching keratin fibers comprising in a cosmetic carrier at least one cationic acyl pyridinium derivative of formula (I)

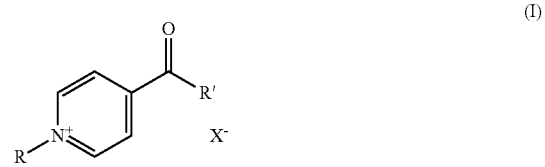

where R is a $C_1$-$C_6$-alkyl group, a $C_2$-$C_6$-alkenyl group, a $C_2$-$C_6$-hydroxy alkyl group, a $C_1$-$C_6$-alkoxy-$C_2$-$C_6$-alkyl group, a carboxy-$C_1$-$C_6$-alkyl group, an aryl-$C_1$-$C_6$-alkyl group, a $C_1$-$C_6$-dialkylamino-$C_2$-$C_6$-alkyl group, a heteroaryl-$C_1$-$C_6$-alkyl group, a 3-oxobutyl group, a 2-oxopropyl group, an aryl group, or a heteroaryl group, R' is a $C_1$-$C_4$-alkyl group, a $C_2$-$C_6$-hydroxy alkyl group, or a $C_1$-$C_6$-alkoxy-$C_2$-$C_6$-alkyl group, X⁻ is a physiologically compatible anion, at least one toxicologically safe co-bleaching activator and/or the physiologically compatible salt thereof, and hydrogen peroxide.

14 Claims, No Drawings

BLEACHING AGENT HAVING CATIONIC ACYL PYRIDINIUM DERIVATIVES, CO-BLEACHING ACTIVATORS AND HYDROGEN PEROXIDE

CROSS REFERENCE TO RELATED APPLICATIONS

The present application is a continuation of International Patent Application No. PCT/EP2009/051835 filed 17 Feb. 2009, which claims priority to German Patent Application No. 10 2008 022 710.2, filed May 7, 2008, both of which are incorporated herein by reference.

The present invention relates to agents for lightening keratin fibers (i.e., agents for use on keratin fibers, particularly human hair) containing cationic acyl pyridinium derivatives, a toxicologically safe co-bleach activator, and hydrogen peroxide for lightening the fibers, as well as to a corresponding method.

Modifying the shape and color of hair is an important area of modern cosmetics. Through modification, the hair's appearance can be adapted both to current fashion trends and to a person's individual wishes. Permanent waves and other methods for modifying hair shape can be applied virtually irrespective of the type of hair treated. In contrast, dyeing and blonding methods are restricted to specific initial hair colors. The principles of blonding methods are known to a person skilled in the art and may be looked up in relevant monographs, for example, by K h. Schräder, Grundlagen and Rezepturen der Kosmetika, 2nd Ed. (1989), Dr. Alfred Hüthig Verlag, Heidelberg, or W. Limbach (ed.), Kosmetik, 2nd Ed. (1995), Georg Thieme Verlag, Stuttgart, New York.

In addition to dyeing, lightening or blonding of natural hair color is desirable to many consumers, since blonde hair color is considered attractive and desirable from a fashion standpoint. A variety of blonding agents of various blonding powers are commercially available for this purpose. Oxidizing agents present in these products lighten hair fibers by oxidative destruction of the hair's own melanin colorant. A moderate blonding effect can be achieved using hydrogen peroxide as the sole oxidizing agent, optionally together with ammonia or other alkalizing agents. If a stronger blonding effect is desired, it is common to use a mixture of hydrogen peroxide and peroxodisulfate salts and/or peroxomonosulfate salts. Lightening is, however, also accompanied by hair damage as it is not only the natural color-imparting components of the hair which suffer oxidative damage, but also other structural components of the hair. Damage can vary from rough, brittle and difficult to comb hair due to reduced resistance and tensile strength of the hair to as far as hair breakage. Typically, the greater the amount of hydrogen peroxide and optional peroxodisulfates used, the more severe the damage caused to the keratin fibers will be. Hair dyes or lightening agents having good lightening power without simultaneously damaging the hair fibers are hitherto unknown.

Before applying onto hair, hair dyes and/or lightening agents are typically mixed with a dilute aqueous hydrogen peroxide solution, resulting in a solid or pasty form. This mixture is then applied onto the hair and subsequently rinsed out after a specific exposure time. The duration of exposure time on the hair required to achieve complete decolorization or lightening is from about 30 to 40 minutes. Obviously, there is a desire among users of these hair dyes or blonding agents to shorten this exposure time.

Blonding processes on keratin fibers accordingly typically occur at alkaline pH values, in particular from 9.0 to 10.5. Alkaline pH values are required to ensure that the external cuticle opens up allowing actives (dye precursors and/or hydrogen peroxide) to penetrate into the hair. A commonly used alkalizing agent is ammonia; however, it often presents an intense odor and possible irritation to the user, which may go as far as causing skin irritation and skin sensitization.

Blonding agents on the market that exhibit good lightening power are not regarded as optimal if they cause hair damage, have long application times and result in skin irritation due to the high concentrations of oxidizing and alkalizing agents.

Use of cationic acyl pyridinium derivatives in hair dyeing is known, for example, from documents DE 10148845 A1 or DE 10261656 A1. In both documents these derivatives are described together with at least a second dyeing component as an agent for dyeing and thus for increasing the color intensity of the hair. Still, it has not hitherto been apparent from the prior art that these 4-acylpyridinium derivatives can be used in specific combination with specific, toxicologically safe co-bleach activators and hydrogen peroxide for bleaching the hair with very good decolorizing action.

Accordingly, the present invention is directed towards novel agents for lightening or blonding hair which are comparable or superior to conventional agents on the market in their lightening power, while at the same time exhibiting reduced hair damage.

It has now been found that use of a combination of cationic acyl pyridinium compounds of general formula (I) (defined below), at least one toxicologically safe co-bleach activator and hydrogen peroxide lightens the hair much more than would be possible by the use of a comparable quantity of hydrogen peroxide alone.

Because of the improved blonding power that the present invention provides, the amount of oxidizing agent used can be reduced, thereby minimizing hair damage. It is also possible to reduce exposure time while achieving a lightening effect similar to the prior art.

Agents according to the invention decolorize the natural colorant melanin by oxidation. In the absence of additional dyes/dye precursors, the active ingredient combination according to the invention does not form any colorant in the keratin-containing fiber. Synthetic dyes previously present on or in the keratin-containing fiber may also be bleached with the assistance of agents according to the invention.

The invention therefore firstly provides an agent for lightening keratin fibers, wherein the agent contains in a cosmetic carrier—

(i) at least one cationic acyl pyridinium derivative according to formula (I)

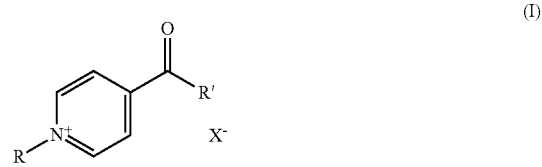

wherein

R is a $C_1$-$C_6$ alkyl group, a $C_2$-$C_6$ alkenyl group, a $C_2$-$C_6$ hydroxyalkyl group, a $C_1$-$C_6$-alkoxy-$C_2$-$C_6$-alkyl group, a carboxy-$C_1$-$C_6$-alkyl group, an aryl-$C_1$-$C_6$-alkyl group, a heteroaryl-$C_1$-$C_6$-alkyl group, a mono- or di-$C_1$-$C_6$-alkylamino-$C_2$-$C_6$-alkyl group, a 3-oxobutyl group, a 2-oxopropyl group, an aryl group or a heteroaryl group;

R' is a $C_1$-$C_4$ alkyl group, a $C_2$-$C_6$ hydroxyalkyl group or a $C_1$-$C_6$-alkoxy-$C_2$-$C_6$-alkyl group; and X⁻ is a physiologically acceptable anion;
(ii) at least one toxicologically safe co-bleach activator and/or the physiologically acceptable salt thereof; and
(iii) hydrogen peroxide.

Keratin fibers include fur, wool, feathers and particularly human hair. Although the present agents are primarily suitable for dyeing and/or lightening keratin fibers, there is no reason in principle why they can not also be used in other fields.

Examples of residues useful as substituents for compounds according to formula (I) are provided hereafter—

Examples of $C_1$-$C_6$-alkyl residues include —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$.

Examples of $C_2$-$C_6$ alkenyl groups includes a prop-2-enyl group (allyl group), a 2-methylprop-2-enyl group, a but-3-enyl group, a but-2-enyl group, a pent-4-enyl group or a pent-3-enyl group. The prop-2-enyl group is particularly preferred in this connection.

Further preferred examples of a $C_2$-$C_6$ hydroxyalkyl group include —$CH_2CH_2OH$, —$CH_2CH_2CH_2OH$, —$CH_2CH(OH)CH_3$, —$CH_2CH_2CH_2CH_2OH$, with the group —$CH_2CH_2OH$ being preferred.

Examples of $C_1$-$C_6$-alkoxy-($C_2$ to $C_6$-alkyl) groups include —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$.

Examples of carboxy-$C_1$-$C_6$ alkyl groups are the carboxymethyl group, the 2-carboxyethyl group or the 3-carboxypropyl group.

Examples of aryl-$C_1$-$C_6$ alkyl groups are the benzyl group and the 2-phenylethyl group.

Examples of heteroaryl-$C_1$-$C_6$ alkyl groups are the pyridin-2-ylmethyl group, the pyridin-3-ylmethyl group, the pyridin-4-ylmethyl group, the pyrimidin-2-ylmethyl group, the pyrrol-1-ylmethyl group, the pyrrol-1-ylethyl group, the pyrazol-1-ylmethyl group or the pyrazol-1-ylethyl group.

Examples of mono- or di-$C_1$-$C_6$-alkylamino-$C_2$-$C_6$ alkyl groups are the 2-methylaminoethyl group, 2-ethylaminoethyl group, 2-dimethylaminoethyl group, 2-diethylaminoethyl group, 3-methylaminopropyl group, 3-dimethylaminopropyl group, 1-piperidinoethyl group, 1-pyrrolidinoethyl group, 4-morpholinoethyl group and 2-bis(2-hydroxyethyl)aminoethyl group, with the 2-dimethylaminoethyl group and the 2-diethylaminoethyl group being particularly preferred.

Examples of an aryl group include the phenyl group, the 1-naphthyl group or the 2-naphthyl group.

Examples of heteroaryl groups are the pyridin-2-yl group, the pyridin-3-yl group, the pyridin-4-yl group, the pyrimidin-2-yl group, the pyrrol-1-yl group, the pyrrol-2-yl group, the pyrazol-1-yl group, the pyrazol-3-yl group or the pyrazol-2-yl group.

Agents according to the invention contain at least three components—at least one cationic acyl pyridinium derivative of the formula (I), at least one toxicologically safe co-bleach activator and/or the physiologically acceptable salt thereof, and hydrogen peroxide. Agents according to the invention also include "application mixtures" (i.e., agents which, although packaged separately (for example for reasons of stability), are mixed together prior to application to form an application mixture and then applied).

Compounds according to formula (I) are preferably suitable if the residue R of general formula (I) is a $C_1$-$C_6$ alkyl group, a $C_2$-$C_6$ alkenyl group or a $C_2$-$C_6$ hydroxyalkyl group.

It is furthermore preferred according to the invention for the residue R' of formula (I) to represent a $C_1$-$C_6$ alkyl group, a $C_2$-$C_6$ alkenyl group, a $C_2$-$C_6$ hydroxyalkyl group, or a $C_1$-$C_6$-alkoxy-$C_2$-$C_6$-alkyl group, particularly a $C_1$-$C_6$ alkyl group (preferably methyl, ethyl, n-propyl or isopropyl).

Preferably the anion X⁻ according to formula (I) is a halide, particularly chloride, bromide and iodide, as well as benzene sulfonate, p-toluene sulfonate, $C_1$-$C_4$ alkyl sulfonate, trifluoromethane sulfonate, acetate, trifluoroacetate, perchlorate, ½ sulfate, hydrogen sulfate, tetrafluoroborate, hexafluorophosphate or tetrachlorozincate. Even more preferably, the physiologically acceptable anion X is a halide ion (particularly chloride or bromide), hydrogen sulfate, ½ sulfate, p-toluene sulfonate, benzene sulfonate or acetate.

Particularly preferred cationic acyl pyridinium derivatives according to general formula (I) Include—

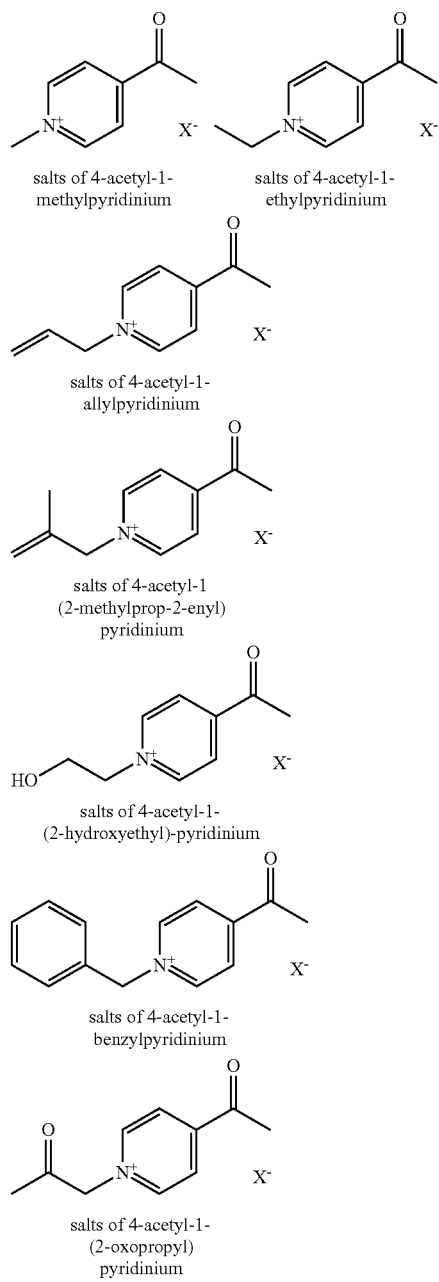

salts of 4-acetyl-1-methylpyridinium salts of 4-acetyl-1-ethylpyridinium salts of 4-acetyl-1-allylpyridinium salts of 4-acetyl-1 (2-methylprop-2-enyl) pyridinium salts of 4-acetyl-1-(2-hydroxyethyl)-pyridinium salts of 4-acetyl-1-benzylpyridinium salts of 4-acetyl-1-(2-oxopropyl) pyridinium

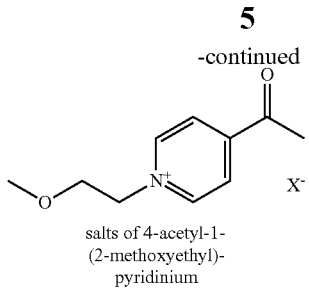

salts of 4-acetyl-1-
(2-methoxyethyl)-
pyridinium wherein X⁻ in each case assumes the meanings according to structure (I) or the meaning of the above-stated preferred embodiments.

To summarize, preferred agents according to the invention include those containing as cationic acyl pyridinium derivative of general structure (I) at least one compound from the group formed from 4-acetyl-1-methylpyridinium p-toluene sulfonate, 4-acetyl-1-methylpyridinium benzene sulfonate, 4-acetyl-1-methylpyridinium bromide, 4-acetyl-1-methylpyridinium hydrogen sulfate, 4-acetyl-1-allylpyridinium p-toluene sulfonate, 4-acetyl-1-allylpyridinium benzene sulfonate, 4-acetyl-1-allylpyridinium bromide, 4-acetyl-1-allylpyridinium hydrogen sulfate, 4-acetyl-1-(2-hydroxyethyl)-pyridinium p-toluene sulfonate, 4-acetyl-1-(2-hydroxyethyl)-pridinium benzene sulfonate, 4-acetyl-1-(2-hydroxyethyl)-pyridinium bromide, 4-acetyl-1-(2-hydroxyethyl)-pyridinium hydrogen sulfate, 4-acetyl-1-(2-oxopropyl)-pyridinium p-toluene sulfonate, 4-acetyl-1-(2-oxopropyl)pyridinium benzene sulfonate, 4-acetyl-1-(2-oxopropyl)pyridinium bromide, 4-acetyl-1-(2-oxopropyl)pyridinium hydrogen sulfate, 4-acetyl-1-ethylpyridinium p-toluene sulfonate, 4-acetyl-1-ethylpyridinium benzene sulfonate, 4-acetyl-1-ethylpyridinium bromide, 4-acetyl-1-ethylpyridinium hydrogen sulfate, -acetyl-1-(2-methylprop-2-enyl)pyridinium p-toluene sulfonate, 4-acetyl-1-(2-methylprop-2-enyl)pyridinium benzene sulfonate, 4-acetyl-1-(2-methylprop-2-enyl)pyridinium bromide, 4-acetyl-1-(2-methylprop-2-enyl)pyridinium hydrogen sulfate, 4-acetyl-1-benzylpyridinium p-toluene sulfonate, 4-acetyl-1-benzylpyridinium benzene sulfonate, 4-acetyl-1-benzylpyridinium bromide, 4-acetyl-1-benzylpyridinium hydrogen sulfate, 4-acetyl-1-(2-methoxyethyl)-pyridinium p-toluene sulfonate, 4-acetyl-1-(2-methoxyethyl)pyridinium benzene sulfonate, 4-acetyl-1-(2-methoxyethyl)pyridinium bromide, 4-acetyl-1-(2-methoxyethyl)pyridinium hydrogen sulfate.

From this group the following acetyl pyridinium salts are very particularly preferred 4-acetyl-1-methylpyridinium p-toluene sulfonate, 4-acetyl-1-methylpyridinium benzene sulfonate, 4-acetyl-1-methylpyridinium bromide, 4-acetyl-1-methylpyridinium hydrogen sulfate, 4-acetyl-1-allylpyridinium p-toluene sulfonate, 4-acetyl-1-allylpyridinium benzene sulfonate, 4-acetyl-1-allylpyridinium bromide, 4-acetyl-1-allylpyridinium hydrogen sulfate, 4-acetyl-1-(2-hydroxyethyl)-pyridinium p-toluene sulfonate, 4-acetyl-1-(2-hydroxyethyl)-pyridinium benzene sulfonate, 4-acetyl-1-(2-hydroxyethyl)-pyridinium bromide, 4-acetyl-1-(2-hydroxyethyl)-pyridinium hydrogen sulfate.

Unless explicitly stated otherwise, all quantities stated below refer to total weight of the ready-to-use agent.

Agents according to the invention contain as a first ingredient acyl pyridinium derivatives according to general structure (I), preferably in an amount of 0.01 to 25 wt. %, particularly 0.1 to 10 wt. %, based on total weight of the ready-to-use agent.

Agents according to the invention contains as a second ingredient at least one toxicologically safe co-bleach activator and/or the physiologically acceptable salt thereof. Imidazole should not be regarded as toxicologically safe for the purposes of the present invention.

Toxicologically safe co-bleach activators are preferably chosen from aliphatic and/or carbocyclic co-bleach activators.

Toxicologically safe co-bleach activators preferably contain a hydroxyl group, a carboxylic acid, a sulfuric acid monoester, a phosphoric acid monoester and/or a physiologically acceptable salt thereof.

If the toxicologically safe co-bleach activator contains a structural unit which allows a plurality of spatial arrangements, such as substituted double bonds or centers of asymmetry, it is understood that all possible stereoisomers are included. It may optionally, however, also be preferred according to the invention to use either just one possible stereoisomer or a mixture of two or more stereoisomers.

Preferred agents according to the invention contain at least one co-bleach activator according to formula (II) and/or the physiologically acceptable salt thereof as co-bleach activator and/or the physiologically acceptable salt thereof—

wherein
Y is a carbonyl group, a direct bond or methylene group,
R1 is hydrogen, a $C_1$-$C_4$ alkyl group, a physiologically acceptable cation or an $SO_3^-$ or a $PO_3^{2-}$ group,
R2 is an amino, a methylamino, a dimethylamino, a trimethylammonio group, phenyl, benzyl, phenoxymethyl, 1-naphthyl, 2-naphthyl, 2-, 3-, 4-toluoyl, or an R4—O—$(CH_2CH_2O)_n$ group, wherein R4 is a $C_6$-$C_{20}$ alkyl group and n is a number 15 or greater,
R3 is hydrogen or an optionally branched $C_1$-$C_6$ alkyl group, provided that,
  if Y is a carbonyl group,
    R1 is hydrogen, a $C_1$-$C_4$ alkyl group or a physiologically acceptable cation,
    R2 is an amino, a methylamino, a dimethylamino or a trimethylammonio group, and
    R3 is hydrogen or an optionally branched $C_1$-$C_6$ alkyl group,
  if Y is a direct bond,
    R1 is hydrogen,
    R2 is phenyl, benzyl, phenoxymethyl, 1-naphthyl, 2-naphthyl, 2-, 3- or 4-toluoyl, and
    R3 is hydrogen or an optionally branched $C_1$-$C_6$ alkyl group,
or
  if Y is a methylene group,
    R1 is an $SO_3^-$ or a $PO_3^{2-}$ group,
    R2 is an R4—$O(CH_2CH_2O)_n$ group, wherein R4 is a $C_6$-$C_{20}$ alkyl group and n is a number greater than 15, and
    R3 is hydrogen.

Preferred agents are particularly characterized in that they contain at least one aliphatic amino acid, optionally N-methylated or N,N-dimethylated on the nitrogen atom thereof, and/or the physiologically acceptable salt thereof as co-bleach activator.

Preferred co-bleach activators include glycine, N-methyl glycine, N,N-dimethyl glycine, alanine, N-methyl alanine, N,N-dimethyl alanine, leucine, N-methyl leucine, N,N-dimethyl leucine, isoleucine, N-methyl isoleucine, N,N-dimethyl isoleucine or the physiologically acceptable salts thereof.

Agents according to the invention more preferably contain glycine and/or the physiologically acceptable salt thereof as co-bleach activator.

Preferred agents according to the invention can contain at least one aromatic alcohol and/or the physiologically acceptable salt thereof as co-bleach activator.

Aromatic alcohols which may be mentioned include benzyl alcohol, 2-phenylethyl alcohol, 1-phenylethyl alcohol, 2-phenoxyethanol, 1-hydroxymethylnaphthalene and/or 2-hydroxymethylnaphthalene.

One aromatic alcohol which is very particularly preferred according to the invention as co-bleach activator is benzyl alcohol.

Finally, agents which may be preferred according to the invention are those which contain as co-bleach activator a physiologically acceptable salt of an alkyl ether sulfate according to formula (III)—

$$R4\text{—}O(CH_2CH_2O)_m SO_3Y \quad (III)$$

wherein R4 is a $C_6$-$C_{20}$ alkyl group; m is a number from 15 or greater; and Y is an alkali metal and/or alkaline earth metal, ammonium, alkylammonium or alkanolammonium Alkyl ether sulfates ("ether sulfates") are manufactured on a large industrial scale by $SO_3$ or chlorosulfonic acid (CSA) sulfation of fatty or oxo alcohol polyglycol ethers and subsequent neutralization. Examples which are preferred according to the invention are sulfates in the form of the sodium and/or magnesium salts of highly ethoxylated addition products of at least 16, averaging 20 to 40 and in particular 25 to 35 mol of ethylene oxide (stated by m in the formula (III)) onto caproic alcohol, caprylic alcohol, 2-ethylhexyl alcohol, capric alcohol, lauryl alcohol, isotridecyl alcohol, myristyl alcohol, cetyl alcohol, stearyl alcohol, isostearyl alcohol, eicosyl alcohol or the technical mixtures thereof. These are obtained, for example, in high pressure hydrogenation of technical methyl esters based on fats and oils or aldehydes from Roelen's oxo synthesis and as a monomer fraction in the dimerization of unsaturated fatty alcohols. Preferred technical fatty alcohols are those with 12 to 18 carbon atoms, such as coconut, palm, palm kernel or tallow fatty alcohol. Ether sulfates can have both a conventional and a narrow homologue distribution. It is particularly preferred to use ether sulfates based on adducts of on average 25 to 35 mol of ethylene oxide onto technical $C_{12/14}$ or $C_{12/18}$ coconut fatty alcohol fractions in the form of the sodium and/or magnesium salts thereof.

One particularly preferred co-bleach activator is known by the INCI name Sodium Coceth-30 Sulfate and is distributed by Cognis as a 31-33 wt. % aqueous solution under the trade name Disponil® FES 77.

The co-bleach activator(s) is/are preferably used within specific ranges. Preferred agents include those having 0.01 to 10 wt. %, particularly 0.1 to 5 wt. %, based on total weight of the ready-to-use agent, of at least one toxicologically safe co-bleach activator.

Agents according to the invention contain hydrogen peroxide as a third ingredient. Hydrogen peroxide is preferably used as an aqueous solution. Hydrogen peroxide can also, however, be used in the form of a solid addition compound of hydrogen peroxide onto inorganic or organic compounds, such as sodium perborate, sodium percarbonate, magnesium percarbonate, sodium percarbamide, polyvinylpyrrolidone n $H_2O_2$ (n is a positive integer greater than 0), urea peroxide and melamine peroxide. In the latter-stated case, the addition compounds liberate hydrogen peroxide in the application mixture according to the invention (i.e., in addition to the addition compound, these agents contain free hydrogen peroxide in the cosmetic carrier).

According to the invention, hydrogen peroxide is very particularly preferably added to the agent as an aqueous hydrogen peroxide solution. The concentration of the hydrogen peroxide solution is determined by statutory requirements, as well as by the desired effect. 6 to 12 wt. % solutions in water are preferably used. Preferred agents contain 0.01 to 12 wt. %, preferably 0.1 to 10 wt. %, particularly preferably 1 to 6 wt. % of hydrogen peroxide (calculated as 100% $H_2O_2$), relative to the total weight thereof.

Considering previously stated preferred embodiments, one specific and preferred embodiment an agent for lightening keratin fibers containing in a cosmetic carrier as a first component at least one compound chosen from 4-acetyl-1-methyl pyridinium p-toluene sulfonate, 4-acetyl-1-methylpyridinium benzene sulfonate, 4-acetyl-1-methylpyridinium bromide, 4-acetyl-1-methylpyridinium hydrogen sulfate, 4-acetyl-1-allylpyridinium p-toluene sulfonate, 4-acetyl-1-allylpyridinium benzene sulfonate, 4-acetyl-1-allylpyridinium bromide, 4-acetyl-1-allylpyridinium hydrogen sulfate, 4-acetyl-1-(2-hydroxyethyl)-pyridinium p-toluene sulfonate, 4-acetyl-1-(2-hydroxyethyl)-pyridinium benzene sulfonate, 4-acetyl-1-(2-hydroxyethyl)-pyridinium bromide and 4-acetyl-1-(2-hydroxyethyl)-pyridinium hydrogen sulfate;

as a second co-bleach activator component at least one compound chosen from glycine, benzyl alcohol and Sodium Coceth-30 Sulfate; and as a third component hydrogen peroxide in the previously mentioned preferred proportions.

Particularly preferred agents include those having one of the following combinations, wherein weight percentages again relate to total weight of the ready-to-use agent—

Combination (a):
0.1 to 4.0 wt. % 4-acetyl-1-methylpyridinium p-toluene sulfonate, 0.1 to 3.0 wt. % glycine and 0.1 to 12.0 wt. % hydrogen peroxide.

Combination (b):
0.1 to 4.0 wt. % 4-acetyl-1-methylpyridinium p-toluene sulfonate, 0.1 to 3.0 wt. % benzyl alcohol and 0.1 to 12.0 wt. % hydrogen peroxide.

Combination (c):
0.1 to 4.0 wt. % 4-acetyl-1-methylpyridinium p-toluene sulfonate, 0.1 to 3.0 wt. % Sodium Coceth-30 Sulfate (active substance) and 0.1 to 12.0 wt. % hydrogen peroxide.

Processes for blonding keratin fibers typically proceed in an alkaline environment. However, an excessively high pH value is not desirable if the keratin fibers and skin are to be treated as gently as possible. Therefore, preferably the pH values of the ready-to-use agent are from 7 to 11, particularly from 8 to 10.5. pH values according to the present invention are pH values which were measured at a temperature of 22° C. Alkalizing agents useful for obtaining the preferred pH value include ammonia, alkali metal hydroxides, alkanolamines, alkali metal metasilicates, alkali metal phosphates and alkali metal hydrogen phosphates. Preferably used alkali metal ions include lithium, sodium and potassium, particularly sodium or potassium. Alkali metal hydroxides usable as an alkalizing agent according to the invention preferably include sodium hydroxide and/or potassium hydroxide.

Alkanolamines usable as an alkalizing agent according to the invention include primary amines with a $C_2$-$C_6$ alkyl parent substance having at least one hydroxyl group. Particularly preferred alkanolamines include 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. Alkanolamines which are very particularly preferred according to the invention include 2-aminoethan-1-ol, 2-amino-2-methylpropan-1-ol and/or 2-amino-2-methylpropane-1,3-diol.

Using only hydrogen peroxide or the addition products thereof onto organic or inorganic compounds is often not sufficient for major lightening of very dark hair. In these cases, a combination of hydrogen peroxide and persulfates or peroxodisulfates is generally used. It has been found that mixing acyl pyridinium derivatives of general structure (I) and toxicologically safe co-bleach activators results in an increase in lightening power, not only with hydrogen peroxide alone, but also with a combination of hydrogen peroxide and persulfate salts or peroxodisulfate salts.

In a further embodiment, should the consumer desire very strong blonding, it may therefore be preferred for the agent to additionally contain at least one inorganic persulfate salt or peroxodisulfate salt in addition to the cationic acyl pyridinium compound of general structure (I), a toxicologically safe co-bleach activator and hydrogen peroxide.

Preferred peroxodisulfate salts include ammonium peroxodisulfate, potassium peroxodisulfate and sodium peroxodisulfate. The peroxodisulfate salts can be present in an amount of 0.1 to 25 wt. %, particularly 0.5 to 15 wt. %, based on total weight of the ready-to-use agent.

As previously mentioned, agents according to the invention can be produced directly before application from two or more separately packaged preparations. This is particularly appropriate for separating incompatible ingredients, thereby avoiding a premature reaction.

One conventional way therefore involves mixing immediately before application a first agent having at least one cationic acyl pyridinium derivative of the general formula (I) and at least one toxicologically safe co-bleach activator with a second agent having an oxidizing agent(s) according to the invention.

The present invention accordingly also provides an agent for lightening keratin fibers, in particular human hair, which is obtained immediately before application onto the hair from a flowable preparation A containing a cationic acyl pyridinium derivatives of general formula (I) and a toxicologically safe co-bleach activator, and an oxidizing agent preparation B containing at least one oxidizing agent chosen from hydrogen peroxide and/or the addition compounds thereof onto organic or inorganic compounds.

Oxidizing agent preparation B is preferably an aqueous, flowable oxidizing agent preparation. Preferred agents according to the invention for lightening keratin fibers include those wherein the flowable oxidizing agent preparation B contains, relative to its weight, 40 to 90 wt. %, preferably 50 to 85 wt. %, particularly preferably 55 to 80 wt. %, more preferably 60 to 77.5 wt. % and in particular 65 to 75 wt. % water.

Persulfate salts or peroxodisulfate salts are generally used in the form of an optionally dedusted powder or in the form of a pressed molding. In order to avoid premature degradation of acyl pyridinium derivatives according to the invention by contact with the persulfate or peroxodisulfates, the persulfates or peroxodisulfates are preferably separately packaged as component C.

The present invention also provides in this connection an agent having 3 components for lightening human hair. This agent is produced immediately before application onto hair by carefully mixing a flowable preparation A containing cationic acyl pyridinium derivatives of general formula (I) and a toxicologically safe co-bleach activator, an oxidizing agent preparation B containing at least one oxidizing agent chosen from hydrogen peroxide and/or the addition compounds thereof onto organic or inorganic compounds, and a third preparation C in powder form containing at least one inorganic persulfate salt or peroxodisulfate salt.

Mixing preparations A and B or, optionally, preparations A, B and C before application results in an application mixture which is an agent according to the invention comprising the three essential ingredients.

An emulsifier or surfactant is preferably added to flowable preparations A and/or B, surface-active substances being designated, depending on the area of application, as surfactants or emulsifiers and chosen from anionic, cationic, zwitterionic, amphoteric and nonionic surfactants and emulsifiers. These substances are described in detail below.

Anionic surfactants suitable in preparations according to the invention include any anionic surface-active substances suitable for use on the human body. These contain an anionic water-solubilizing group such as a carboxylate, sulfate, sulfonate or phosphate group and a lipophilic alkyl group with approximately 8 to 30 C atoms. The molecule may additionally contain glycol or polyglycol ether groups, ester, ether and amide groups and hydroxyl groups. Examples of suitable anionic surfactants include, in each case in the form of sodium, potassium, ammonium and the mono-, di- and trialkanol ammonium salts with 2 to 4 C atoms in the alkanol group, linear and branched fatty acids (soaps), ether carboxylic acids of the formula $RO(CH_2CH_2O)_xCH_2COOH$, acyl sarcosides, acyl taurides, acyl isethionates, optionally polyalkoxylated sulfosuccinic acid mono- and dialkyl esters, linear alkane sulfonates, linear α-olefin sulfonates, sulfonates of unsaturated fatty acids, α-sulfofatty acid methyl esters, alkyl sulfates and alkyl ether sulfates of the formula $RO(CH_2CH_2O)_xSO_3H$, mixtures of surface-active hydroxysulfonates, sulfated hydroxyalkyl polyethylene glycol ethers and/or hydroxyalkylene propylene glycol ethers, esters of tartaric acid and citric acid with alcohols, alkyl and/or alkenyl ether phosphates, sulfated fatty acid alkylene glycol esters of the formula $RC(O)O(alkO)_nSO_3H$ and monoglyceride sulfates and monoglyceride ether sulfates.

Zwitterionic surfactants are those surface-active compounds having at least one quaternary ammonium group and at least one carboxylate, sulfonate or sulfate group per molecule. Particularly suitable zwitterionic surfactants include "betaines" such as N-alkyl N,N-dimethyl ammonium glycinates (e.g., cocoalkyldimethyl ammonium glycinate), N-acylaminopropyl-N,N-dimethyl ammonium glycinates (e.g., cocoacylaminopropyldimethyl ammonium glycinate), and 2-alkyl-3-carboxymethyl-3-hydroxyethylimidazolines with in each case 8 to 18 C atoms in the alkyl or acyl group and cocoacylaminoethylhydroxyethylcarboxymethyl glycinate. A preferred zwitterionic surfactant is the fatty acid amide derivative known by the INCI name Cocamidopropyl Betaine.

Amphoteric surfactants include surface-active compounds which, in addition to a $C_8$-$C_{24}$ alkyl or acyl group, contain at least one free amino group and at least one —COOH or —SO$_3$H group per molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case approximately 8 to 24 C atoms in the alkyl group. Particularly preferred amphoteric surfactants are N-cocoalkyl aminopropionate, cocoacylaminoethyl aminopropionate and $C_{12}$-$C_{18}$ acyl sarcosine.

It is further advantageous for lightening agents according to the invention to contain non-ionogenic, interfacially active substances. Nonionic surfactants can contain as a hydrophilic group, for example, a polyol group, a polyalkylene glycol ether group or a combination of a polyol and polyalkylene glycol ether group. Such compounds include—

- addition products of 2 to 50 mol of ethylene oxide and/or 0 to 5 mol of propylene oxide onto linear and branched fatty alcohols with 8 to 30 C atoms, onto fatty acids with 8 to 30 C atoms and onto alkylphenols with 8 to 15 C atoms in the alkyl group;
- addition products, end group-terminated with a methyl or $C_2$-$C_6$ alkyl residue, of 2 to 50 mol of ethylene oxide and/or 0 to 5 mol of propylene oxide onto linear and branched fatty alcohols with 8 to 30 C atoms, onto fatty acids with 8 to 30 C atoms and onto alkylphenols with 8 to 15 C atoms in the alkyl group;
- $C_{12}$-$C_{30}$ fatty acid mono- and diesters of addition products of 1 to 30 mol of ethylene oxide onto glycerol;
- polyglycerol esters and alkoxylated polyglycerol esters;
- addition products of 5 to 60 mol of ethylene oxide onto castor oil and hardened castor oil;
- polyol fatty acid esters;
- alkoxylated, preferably propoxylated and in particular ethoxylated, mono-, di- and triglycerides, such as glycerol monolaurate +20 ethylene oxide and glycerol monostearate +20 ethylene oxide;
- alkoxylated fatty acid alkyl esters of the formula RC(O)—(OCH$_2$CH$_2$)$_w$OR', wherein RC(O)— is a linear or branched, saturated and/or unsaturated acyl residue with 6 to 22 carbon atoms, R' is linear or branched alkyl residues with 1 to 4 carbon atoms and w is a number from 1 to 20;
- amine oxides;
- hydroxy mixed ethers;
- sorbitan fatty acid esters and addition products of ethylene oxide onto sorbitan fatty acid esters such as for example polysorbates, sorbitan monolaurate and sorbitan monolaurate +20 mol ethylene oxide (EO);
- sugar fatty acid esters and addition products of ethylene oxide onto sugar fatty acid esters;
- addition products of ethylene oxide onto fatty acid alkanolamides and fatty amines;
- fatty acid N-alkylglucamides;
- alkylphenols and alkylphenol alkoxylates with 6 to 21, in particular 6 to 15, carbon atoms in the alkyl chain and 0 to 30 ethylene oxide and/or propylene oxide units. Preferred representatives of this class include nonylphenol +4 EO, nonylphenol +9 EO, octylphenol +3 EO and octylphenol +8 EO; and
- alkyl polyglycosides corresponding to the general formula RO—(Z)$_x$, wherein R is alkyl, Z is a sugar and x is the number of sugar units. Alkyl polyglycosides usable according to the invention can contain only one specific alkyl residue R.

Suitable nonionic surfactants are in particular $C_8$-$C_{22}$ alkyl mono- and oligoglycosides and the ethoxylated analogues thereof. Non-ethoxylated compounds have proved particularly suitable.

These compounds are characterized in that any desired mono- or oligosaccharides may be used as the sugar building block Z. Sugars with 5 or 6 carbon atoms and the corresponding oligosaccharides are conventionally used. Such sugars include glucose, fructose, galactose, arabinose, ribose, xylose, lyxose, allose, altrose, mannose, gulose, idose, talose and sucrose. Preferred sugar building blocks are glucose, fructose, galactose, arabinose and sucrose, with glucose being particularly preferred.

Alkyl polyglycosides usable according to the invention contain on average 1.1 to 5 sugar units. Alkyl polyglycosides with x values of 1.1 to 2.0 are preferred. Alkyl glycosides wherein x is 1.1 to 1.8 are very particularly preferred.

Alkoxylated homologues of the stated alkyl polyglycosides may also be used according to the invention. These homologues may contain on average up to 10 ethylene oxide and/or propylene oxide units per alkyl glycoside unit.

Further preferred nonionic surfactants include alkylene oxide addition products onto saturated linear fatty alcohols and fatty acids with in each case 2 to 30 mol of ethylene oxide per mol of fatty alcohol or fatty acid respectively. Preparations having excellent properties are obtained if they contain fatty acid esters of ethoxylated glycerol as the nonionic surfactants.

Particularly preferred nonionogenic surface-active substances include, due to ease of processing, substances which are commercially available in pure form as solids or liquids. Purity here does not refer to chemically pure compounds. The term purity instead refers in this connection to the fact that the selected substances should preferably contain no solvents, adjusting agents and other accompanying substances. Particularly in relation to naturally based products, mixtures of different homologs may be used, for example, with different alkyl chain lengths, as are obtained in the case of products based on natural fats and oils. For alkoxylated products also, mixtures of differing degrees of alkoxylation can also be present.

Surfactants which are addition products of ethylene and/or propylene oxide onto fatty alcohols or derivatives of these addition products may be used both as products with a "normal" homolog distribution and as products with a narrow homolog distribution. A "normal" homolog distribution refers to mixtures of homologs obtained by reacting fatty alcohol and alkylene oxide using alkali metals, alkali metal hydroxides or alkali metal alkoxides as catalysts. Narrow homolog distributions, in contrast, are obtained if hydrotalcite, alkaline earth metal salts of ether carboxylic acids, alkaline earth metal oxides, hydroxides or alkoxides are, for example, used as catalysts. It may be preferred to use products with a narrow homolog distribution.

Anionic, nonionic, zwitterionic or amphoteric surfactants are used in amounts of 0.1 to 45 wt. %, preferably 1 to 30 wt. % and more preferably 1 to 15 wt. %, based on total weight of the ready-to-use agent.

According to the invention, preference is likewise given to cationic surfactants of the quaternary ammonium compound, ester quat and amidoamine type. Preferred quaternary ammonium compounds are ammonium halides, in particular chlorides and bromides, such as alkyltrimethylammonium chlorides, dialkyldimethylammonium chlorides and trialkylmethylammonium chlorides, for example cetyltrimethylammonium chloride, stearyltrimethylammonium chloride, distearyldimethyl ammonium chloride, lauryldimethylammonium chloride, lauryldimethylbenzylammonium chloride and tricetylmethylammonium chloride, and the imidazolinium compounds known under the INCI names Quaternium-27 and Quaternium-83. The long alkyl chains of the above-stated surfactants preferably comprise 10 to 18 carbon atoms. Quaternized protein hydrolysates are further cationic surfactants which are usable according to the invention.

Alkylamidoamines are conventionally produced by amidating natural or synthetic fatty acids and fatty acid cuts with dialkylaminoamines and, in addition to a good conditioning action, are specifically distinguished by having good biodegradability.

Quaternary ester compounds ("ester quats") are likewise very readily biodegradable. Ester quats are known substances which contain both at least one ester function and at least one quaternary ammonium group as a structural element. Preferred ester quats include quaternized ester salts of fatty acids with triethanolamine, quaternized ester salts of fatty acids with diethanolalkylamines and quaternized ester salts of fatty acids with 1,2-dihydroxypropyldialkylamines.

Agents used according to the invention preferably contain cationic surfactants in amounts of 0.05 to 10 wt. %, relative to the total agent. Quantities of 0.1 to 5 wt. % are particularly preferred.

In one preferred embodiment, nonionic, zwitterionic and/or amphoteric surfactants and mixtures thereof may be preferred.

In a further preferred embodiment, the action of the active ingredient according to the invention may be enhanced by emulsifiers. Such emulsifiers are for example Agents according to the invention preferably contain emulsifiers in amounts of 0.1 to 25 wt. %, particularly 0.5 to 15 wt. %, based on total amount of the ready-to-use agent.

Compositions according to the invention may preferably contain at least one nonionogenic emulsifier with an HLB value of 8 to 18 in accordance with the definitions provided in Römpp-Lexikon Chemie (eds. J. Falbe, M. Regitz), 10th Ed., Georg Thieme Verlag Stuttgart, New York, (1997), p. 1764. Nonionogenic emulsifiers with an HLB value of 10-15 may be particularly preferred according to the invention.

Among the stated types of emulsifiers, those emulsifiers containing no ethylene oxide and/or propylene oxide in their molecule may be very particularly preferred.

Agents according to the invention may further contain dyes and/or dye precursors and thus be provided as agents having simultaneous lightening and coloring action. Such agents are hereinafter referred to as "dye preparations", "lightening dye preparations" or "dyeing and lightening agents".

Oxidative dyeing of the fibers in the presence of oxidation dye precursors can occur with atmospheric oxygen. Preferably, however, a chemical oxidizing agent is used, particularly when it is desirable to lighten human hair as well as dye it. This lightening effect may be desired independently of the dyeing method. Useful oxidizing agents include persulfates, chlorites and, in particular, hydrogen peroxide or the addition products thereof onto urea, melamine, as well as sodium borate.

According to the invention, however, the oxidation dye preparation can also be applied onto the hair in combination with a catalyst which activates the oxidation of the dye precursors, for example, by atmospheric oxygen. Such catalysts include specific enzymes, iodides, quinones or metal ions.

Suitable enzymes include peroxidases capable of distinctly enhancing the action of small quantities of hydrogen peroxide. Other suitable enzymes include those which, with the assistance of atmospheric oxygen, directly oxidize the oxidation dye precursors, such as laccases, or which produce small quantities of hydrogen peroxide in situ and so biocatalytically activate oxidation of the dye precursors. Particularly suitable catalysts for the oxidation of dye precursors are "two-electron oxidoreductases" in combination with their specific substrates, pyranose oxidase (with, for example, D-glucose or galactose), glucose oxidase (with D-glucose), glycerol oxidase (with glycerol), pyruvate oxidase (with pyruvic acid or the salts thereof), alcohol oxidase (with alcohol such as MeOH, EtOH), lactate oxidase (with lactic acid), tyrosinase-oxidase (with tyrosine), uricase (with uric acid), choline oxidase (with choline) and amino acid oxidase (with amino acids).

When additional oxidizing agents are used, the actual lightening agent and/or dye preparation is conveniently produced immediately before application by mixing the additional oxidizing agent preparation with the hydrogen peroxide solution according to the invention and with the preparation containing the compounds of the formula (I) and the toxicologically safe co-bleach activator and optionally dye precursors. The resultant ready-to-use lightening agent and/or hair dye preparation should preferably have a pH value in the range from 6 to 12. It is particularly preferred to apply the lightening agent and/or hair dye preparation in a weakly alkaline environment. Application temperatures may be in a range between 15 and 40° C. After an exposure time of 5 to 45 minutes, the hair dye is rinsed out of the hair. Rewashing with a shampoo is not required if a cosmetic carrier with an elevated surfactant content (e.g., a coloring shampoo) has been used.

For hair which is difficult to dye, however, an agent according to the invention optionally comprising additional dye precursors may also be applied onto the hair without prior mixing with the oxidation component. After an exposure time of 20 to 30 minutes, optionally after intermediate rinsing, the oxidation component mixed with the preparation containing acyl pyridinium derivative according to formula (I) and the toxicologically safe co-bleach activator is applied. After a further exposure time of 10 to 20 minutes, the hair is then rinsed and reshampooed if desired. According to a first variant of this embodiment, wherein prior application of the dye precursors is intended to bring about better penetration into the hair, the corresponding agent is adjusted to a pH value of approx. 4 to 7. According to a second variant, atmospheric oxidation is initially sought, the applied agent preferably having a pH value of 7 to 10. The additional use of acidified peroxodisulfate solutions as oxidizing agent may be preferred for the subsequent accelerated post-oxidation.

It may also be preferred to use specific metal ions or complexes in order to obtain intense dyed colors. Suitable metal ions are for example $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$, $Ce^{4+}$, $V^{3+}$, $Co^{2+}$, $Ru^{3+}$ and $Al^{3+}$, $Zn^{2+}$, $Cu^{2+}$ and $Mn^{2+}$ are here particularly suitable. The metal ions can be used in the form of any desired, physiologically acceptable salt or in the form of a complex compound. Preferred salts are acetates, sulfates, halides, lactates and tartrates. By using these metal salts, it is possible to both accelerate dye formation and have a targeted influence on color shade.

Particularly preferred agents contain 0.0001 to 2.5 wt. %, preferably 0.001 to 1 wt. %, of at least one compound from the group copper chloride ($CuCl_2$), copper sulfate ($CuSO_4$), iron (II) sulfate, manganese(II) sulfate, manganese(II) chloride, cobalt(II) chloride, cerium sulfate, cerium chloride, vanadium sulfate, manganese dioxide ($MnO_2$).

It is also preferred according to the invention to use "complexing agents". Complexing agents are substances capable of complexing metal ions. Preferred complexing agents are "chelate" complexing agents, namely, substances which form cyclic compounds with metal ions, one individual ligand having more than one coordination site on a central atom (i.e., being at least "bidentate"). Here, extended compounds are normally closed into rings by complexation via an ion. The number of bound ligands depends on the coordination number of the central ion.

Any prior art complexing agents may be used for the purposes of the present invention and may belong to different chemical groups. The following are preferably used individually or in combination with one another— polycarboxylic acids in which the total of carboxyl and optionally hydroxyl groups is at least 5, such as gluconic acid;
  nitrogen-containing mono- or polycarboxylic acids such as ethylenediaminetetraacetic acid (EDTA), N-hydroxyethylethylenediaminetriacetic acid, diethylenetriaminepentaacetic acid, hydroxyethyliminodiacetic acid, nitrilodiacetic acid-3-propionic acid, isoserinediacetic acid, N,N-di-(2-hydroxyethyl)glycine, N-(1,2-dicarboxy-2-hydroxyethyl)-glycine, N-(1,2-dicarboxy-2-hydroxyethyl)-aspartic acid or nitrilotriacetic acid (NTA);
  geminal diphosphonic acids such as 1-hydroxyethane-1,1-diphosphonic acid (HEDP), the higher homologues thereof with up to 8 carbon atoms together with derivatives thereof containing hydroxy or amino groups and 1-aminoethane-1,1-diphosphonic acid, the higher homologues thereof with up to 8 carbon atoms together with derivatives thereof containing hydroxy or amino groups;
  aminophosphonic acids such as ethylenediaminetetra(methylenephosphonic acid), diethylenetriaminepenta(methylenephosphonic acid) or nitrilotri(methylenephosphonic acid);
  phosphonopolycarboxylic acids such as 2-phosphonobutane-1,2,4-tricarboxylic acid; and
  cyclodextrins.

Preferred complexing agents include phosphonates, preferably hydroxyalkane- or aminoalkanephosphonates and particularly 1-hydroxyethane-1,1-diphosphonate (HEDP) or the di- or tetrasodium salt thereof and/or ethylenediaminetetramethylenephosphonate (EDTMP) or the hexasodium salt thereof and/or diethylenetriaminepentamethylenephosphonate (DTPMP) or the hepta- or octasodium salt thereof.

As previously mentioned, agents according to the invention can be in the form of pure lightening agents (i.e., as "blonding agents"), as well as dyeing and lightening agents that also effect dyeing of the keratin fibers simultaneously with the lightening.

Depending on the requirements placed on the dyed color, a person skilled in the art is aware of various dyeing systems for providing color-modifying cosmetics, particularly for skin or keratin-containing fibers such as human hair.

"Oxidation dye preparations", as they are known, are used for permanent, high intensity dyed colors with corresponding fastness characteristics. Such dye preparations conventionally contain oxidation dye precursors (i.e., "developer components" and "coupler components"). Under the influence of oxidizing agents or atmospheric oxygen, developer components develop the actual dyes through action with one another or by coupling with one or more coupler components. Oxidation dye preparations are distinguished by excellent, long-lasting dyeing results. A mixture of a relatively large number of oxidation dye precursors must, however, normally be used if natural looking dyed colors are to be obtained; in many cases, direct dyes are additionally used for shading purposes.

For temporary dyeing, dyes or tints containing "direct" dyes as the coloring component are typically used. These are dye molecules which key directly to the substrate and do not need an oxidative process to develop the color. These dyes include henna, which has been known since antiquity for dyeing bodies and hair. These dyed colors are in general distinctly more sensitive to shampooing than are oxidatively dyed colors, such that an often unwanted shift in shade or even a visible, uniform color loss then occurs very much more quickly.

Finally, another dyeing method that has attracted considerable attention involves applying precursors of the hair's natural colorant melanin onto the substrate (e.g., hair). These then form nature-analogous dyes in the context of oxidative processes in the hair. In multiple application of agents containing 5,6-dihydroxyindoline, it is possible to return gray human hair to its natural color. Coloration may then proceed with atmospheric oxygen as the sole oxidizing agent, such that no further oxidizing agent has to be used. For individuals with originally medium blonde to brown hair, indoline may be used as sole dye precursor. For individuals with originally red, and particularly dark to black hair color, satisfactory results are often only achieved by using further dye components with it, in particular specific oxidation dye precursors.

In one embodiment for color modification, the subject matter of the present invention may be combined with at least one color-modifying component. Color-modifying components for the purposes of the present invention are preferably chosen from (1) at least one oxidation dye precursor and/or (2) at least one direct dye.

For this purpose, such agents according to the invention contain at least one dye precursor, preferably an oxidation dye precursor and/or at least one direct dye. Among these, "oxidation dye preparations" are in particular preferred.

Oxidation dye preparations according to the invention contain at least one coupler component and at least one developer component. The coupler and developer components are also known as oxidation dye precursors. Oxidation dye preparations according to the invention may also additionally contain direct dyes as shading agents.

Preferred agents for dyeing and/or lightening keratin fibers contain at least one oxidation dye precursor of the developer type and/or of the coupler type.

Preferred developer components include at least one compound from p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts of these compounds.

With respect to oxidative dyeing, coupler components alone do not form any significant dyed color, but instead can require the presence of developer components. It is therefore preferred according to the invention that, when at least one developer component is used, at least one coupler component is additionally used.

Particularly preferred coupler components include m-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy) ethanol, 1,3-bis-(2,4-diaminophenoxy)propane, 1-methoxy-2-amino-4-(2'-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl) amino]-2-methoxy-5-methylphenyl}amino)ethanol, 2-({3-[(2-hydroxyethyl)amino]-4,5-dimethylphenyl}amino) ethanol, 2-[3-morpholin-4-ylphenyl)amino]ethanol, 3-amino-4-(2-methoxyethoxy)-5-methylphenylamine, 1-amino-3-bis-(2'-hydroxyethyp-aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts of the above-stated compounds.

Developer and coupler components are preferably used in an amount of 0.005 to 20 wt. %, preferably 0.1 to 5 wt. %, based on total weight of the ready-to-use oxidation dye preparation.

Developer components and coupler components are generally used in approximately molar quantities relative to one another. While molar use has also proven convenient, a certain excess of individual oxidation dye precursors is not disadvantageous, such that developer components and coupler components may be present in a molar ratio of 1:0.5 to 1:3, in particular 1:1 to 1:2.

Agents according to the invention can also contain at least one direct dye. These are dyes which key directly to the hair and do not need an oxidative process to develop the color. Direct dyes include nitrophenylenediamines, nitroaminophenols, azo dyes, anthraquinones or indophenols.

Direct dyes are preferably used in an amount of 0.001 to 20 wt. %, relative to the entire ready-to-use preparation. The total amount of direct dyes is preferably no more than 20 wt. %.

Direct dyes may be subdivided into anionic, cationic and nonionic direct dyes. Preferred anionic direct dyes are the compounds known by the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52. Preferred cationic direct dyes are here cationic triphenylmethane dyes, such as Basic Blue 7, Basic Blue 26, Basic Violet 2 and Basic Violet 14; aromatic systems which are substituted with a quaternary nitrogen group, such as Basic Yellow 57, Basic Red 76, Basic Blue 99, Basic Brown 16 and Basic Brown 17, and direct dyes containing a heterocycle which comprises at least one quaternary nitrogen atom, as are mentioned, for example, in claims 6 to 11 of EP-A2-998 908. Compounds also known by the names Basic Yellow 87, Basic Orange 31 and Basic Red 51 are very particularly preferred cationic direct dyes. Cationic direct dyes distributed under the trademark Arianor® are very particularly preferred cationic direct dyes according to the invention. Suitable nonionic direct dyes include nonionic, nitro and quinone dyes and neutral azo dyes. Preferred nonionic direct dyes include the compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2'-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

It is not necessary for the direct dyes to be uniform compounds. Instead, as a result of the production processes for the individual dyes, subordinate quantities of still further components may be present, provided that these do not have a disadvantageous effect on the dyeing result or have to be excluded for other reasons, for example, toxicological reasons.

Naturally occurring dyes may furthermore also be used as direct dyes, such as are present in henna red, henna neutral, henna black, chamomile flowers, sandalwood, black tea, alder buckthorn bark, sage, logwood, madder root, catechu and alkanet root.

Agents according to the invention can further contain active ingredients, auxiliary substances and additives, such as nonionic polymers, cationic polymers, zwitterionic and amphoteric polymers, anionic polymers, thickeners, structuring agents, hair-conditioning compounds, protein hydrolysates, perfume oils, dimethyl isosorbide and cyclodextrins, active ingredients which improve fiber structure, defoamers such as silicones, dyes for coloring the agent, antidandruff active ingredients such as piroctone olamine, zinc omadine and climbazole, light stabilizers, in particular derivatives of benzophenone, cinnamic acid and triazine, active ingredients such as panthenol, pantothenic acid, pantolactone, allantoin, pyrrolidinone carboxylic acids and the salts thereof and bisabolol, vitamins, provitamins and vitamin precursors, in particular those of groups A, $B_3$, $B_5$, $B_6$, C, E, F and H, plant extracts, cholesterol, consistency providers such as sugar esters, polyol esters or polyol alkyl ethers, fats and waxes such as spermaceti, beeswax, montan wax and paraffins, fatty acid alkanolamides, swelling and penetrating substances, opacifiers such as latex, styrene/PVP and styrene/acrylamide copolymers, pearlescent agents, pigments, stabilizers for hydrogen peroxide and other oxidizing agents, propellants such as propane-butane mixtures, N$_2$O, dimethyl ether, CO$_2$ and air, antioxidants.

A person skilled in the art can select these additional substances based on the desired properties of the agents.

With regard to further optional components and the amounts used, reference is made to relevant handbooks known to a person skilled in the art, for example, K h. Schräder, Grundlagen and Rezepturen der Kosmetika, 2nd Ed., Hüthig Buch Verlag, Heidelberg (1989).

Compositions according to the invention may contain as a further component at least one ammonium compound from the group ammonium chloride, ammonium carbonate, ammonium bicarbonate, ammonium sulfate and/or ammonium carbamate in an amount of 0.5 to 10, preferably 1 to 5 wt. %, relative to the total composition of the agent.

Agents according to the invention can contain active ingredients in a cosmetic carrier. This cosmetic carrier is preferably aqueous, alcoholic or aqueous-alcoholic. Carriers suitable for the purpose of hair bleaching include creams, emulsions or gels, as well as surfactant-containing foaming solutions such as shampoos, foam aerosols or other preparations suitable for use on the hair. It is, however, also possible to provide a formulation in powdered or tablet form, this being preferred for lightening agents. Prior to application, this formulation is mixed in a solvent such as water, or with organic solvents or mixtures of water and organic solvents to obtain the application mixture.

An aqueous carrier preferably contains for the purposes of the invention at least 40 wt. %, particularly at least 50 wt. %, water.

For the purposes of the present invention, aqueous-alcoholic solutions refer to aqueous solutions containing 3 to 70 wt. % of a C$_1$-C$_4$ alcohol, particularly ethanol or isopropanol. Agents according to the invention may additionally contain further organic solvents such as methoxybutanol, ethyldiglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred for this purpose.

Preferred agents according to the invention can additionally contain a nonaqueous solvent, with particularly preferred agents containing the solvent in a concentration of 0.1-30 wt. %, preferably 1-20 wt. %, even more preferably 2-10 wt. %, relative to the agent.

The present invention secondly provides a method for lightening keratin fibers, in particular human hair, wherein an agent as described above is applied onto keratin-containing fibers, left on the fibers for 5 to 60 minutes and then rinsed back out or washed out with a shampoo. Preferably, the temperature during the exposure time of 5 to 60 minutes is from 10° C. to 40° C., particularly 20° C. to 38° C.

For the purposes of such a method, it may be preferred to describe the method as follows:
  if desired, a pretreatment agent M1 is applied onto the fibers;
  an agent M2 is then used on the fibers with, if desired, a further agent M3 being added to the agent M2 prior to use;
  agent M2 is rinsed off the fibers after a period of 5-60 minutes; and
  after the treatment a post-treatment agent M4 is optionally applied to the fibers and rinsed off again after an exposure time of a few minutes;
  wherein at least one of the agents M1, M2 or M3 or mixture of agents M2 and M3 being an agent according to the invention of the first subject matter of the invention.

Agents according to the invention may thus be formulated as single component agents (dye preparation and/or lightening agent M2), as two-component agents (M2+M3), and used accordingly. Separation into multi-component systems can be considered where incompatibilities of the ingredients are to be expected or feared. In such systems, the agent for use is produced by the consumer directly before application by mixing the components.

A dyeing and/or lightening method in which the compounds of the general structure (I) and the co-bleach activator are initially present separate from hydrogen peroxide is here preferred. The present invention accordingly also provides a method for lightening and optionally dyeing human hair, in which a water-based composition containing hydrogen peroxide is mixed with a composition containing at least one compound of the general structure (I) and at least one toxicologically safe co-bleach activator (see above) to form an agent of the first subject matter of the invention and the latter is applied onto the hair.

A further embodiment of the method according to the invention for lightening and optionally dyeing human hair involves mixing a water-based composition containing hydrogen peroxide with an agent preferably containing at least one alkalinity donor and/or direct hair dye and/or at least one oxidation dye precursor and an agent containing a compound according to general structure (I) (see above) and additionally a co-bleach activator (see above) to form a homogeneous composition, and then applying the mixture onto the hair.

The present invention thirdly provides the use of the agent described above for lightening keratin-containing fibers, particularly human hair.

With regard to further preferred embodiments of the method according to the invention or of the use according to the invention, the statements made regarding agents according to the invention apply mutatis mutandis.

EXAMPLES 1.0-Synthesis of 4-acetyl-1-methylpryidinium p-toluene sulfonate-

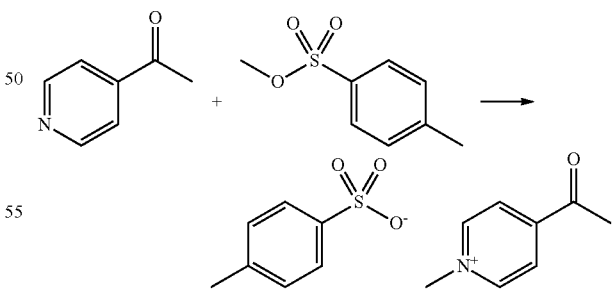

30.0 g (0.25 mol) of 4-acetylpyridine and 55.8 g (0.30 mol) of p-toluene sulfonic acid methyl ester were heated to reflux for 5 hours in 500 ml of ethanol. The solvent was stripped out under a vacuum in a rotary evaporator and the residue digested with ether. After separating the ether phase, the product gradually crystallized out. The product was dried under a vacuum. Yield: 59.9 g (82.5%); $^1$H-NMR (400 MHz. DMSO-d6): δ [ppm]=2.26 (s, 3H); 2.72 (s, 3H); 3.39 (s, 3H);

7.11 (d, 2H); 7.49 (d, 2H); 8.42 (d, 2H); 9.20 (d, 2H); $^{13}$C-NMR (400 MHz, DMSO-d6): δ [ppm]=20.8; 26.4; 48.1; 124.8; 125.3; 127.7; 138.9; 145.2; 146.5; 148.3; 195.8.

2.0-Examples of Blonding- 2.1. Blonding with Hydrogen Peroxide and Co-bleach Activator 2.1.1. Production of a Blonding Cream Blonding creams were produced as follows from the listed components

|  | wt. % | | | | |
|---|---|---|---|---|---|
| Raw material | comp. 1 | comp. 2 | inv. 1 | inv. 2 | inv. 3 |
| Hydrenol D | .9 | .9 | .9 | .9 | .9 |
| Lorol technical | .5 | .5 | .5 | .5 | .5 |
| Eumulgin B1 | .6 | .6 | .6 | .6 | .6 |
| Eumulgin B2 | .6 | .6 | .6 | .6 | .6 |
| Akypo Soft 45 NV | 0.0 | 0.0 | 0.0 | 0.0 | 0.0 |
| Plantacare 1200 UP | .0 | .0 | .0 | .0 | .0 |
| Texapon K14 S 70 C | .8 | .8 | .8 | .8 | .8 |
| Ammonium sulfate | .0 | .0 | .0 | .0 | .0 |
| Ascorbic acid | .1 | .1 | .1 | .1 | .1 |
| Sodium silicate 40/42 | .5 | .5 | .5 | .5 | .5 |
| Turpinal SL | .2 | .2 | .2 | .2 | .2 |
| KOH | .8 | .8 | .8 | .8 | .8 |
| Ammonia, 25 wt. % aqueous | .1 | .1 | .1 | .1 | .1 |
| Glycine | — | — | .0 | — | — |
| Benzyl alcohol | — | — | — | .0 | — |
| Disponil FES 77 (active substance) | — | — | — | — | .0 |
| 4-Acetyl-1-methylpyridinium p-toluene sulfonate (according to Example 1.1) | — | .0 | .0 | .0 | .0 |
| Water | ad 100 | ad 100 | ad 100 | ad 100 | ad 100 |

| | |
|---|---|
| Hydrenol ® D | C$_{16}$-C$_{18}$ fatty alcohol (INCI name: Cetearyl Alcohol) (Cognis) |
| Lorol ® technical | C$_{12}$-C$_{18}$ fatty alcohol (INCI name: Coconut Alcohol) (Cognis) |
| Eumulgin ® B1 | C$_{16}$-C$_{18}$ fatty alcohol, ethoxylated (12 EO) (INCI name: Ceteareth-12) (Cognis) |
| Eumulgin ® B2 | C$_{16}$-C$_{18}$ fatty alcohol, ethoxylated (20 EO) (INCI name: Ceteareth-20) (Cognis) |
| Akypo ® Soft 45 NV | C$_{12}$-C$_{14}$ fatty alcohol ether acetic acid, sodium salt (4.5 EO) (INCI name: Sodium Laureth-5 Carboxylate) (KAO Chemicals) |
| Plantacare ® 1200 UP | C$_{12}$-C$_{16}$ fatty alcohol glucoside (INCI name: Lauryl Glucoside) (Cognis) |
| Texapon ® K14 S 70 C | Myristyl ether sulfate, sodium salt (approx. 70% active substance; INCI name: Sodium Myreth Sulfate) (Cognis) |
| Turpinal ® SL | 1-Hydroxyethane-1,1-diphosphonic acid (approx. 60% active substance content; INCI name: Etidronic Acid, Aqua (Water)) (Solutia) |
| Sodium silicate 40/42 | Soda water glass |
| Disponil ® FES 77 | C$_{12}$-C$_{18}$ fatty alcohol ether sulfate, sodium salt (30 EO) (approx. 31-33% active substance in water; INCI name: Sodium Coceth-30 Sulfate) (Cognis) |

Hydrenol D, Loral, Eumulgin B1, Eumulgin B2, Akypo Soft 45 NV, Plantacare 1200 UP and Texapon K 14 S 70 C were melted together at 80° C. and dispersed with part of the water. The remaining ingredients of the formulation were then stirred in in succession. The formulation was then made up to 100 wt. % with water and stirred until cold.

Formulations comp. 1 and comp. 2 are comparison formulations not according to the invention without co-bleach activator; formulations inv. 1 to inv. 3 are examples according to the invention with the bleach activator 4-acetyl-1-methylpyridinium p-toluenesulfonate and co-bleach activators.

2.1.2-Mixing with Developer Dispersion

Each blonding cream was thoroughly mixed in a 1:1 ratio with a developer dispersion of the following composition. The pH value of the finished application mixture was from 9 to 10.2.

| Raw material | wt. % |
|---|---|
| Ammonia, 25% | 0.62 |
| Dipicolinic acid | 0.10 |
| Disodium pyrophosphate | 0.03 |
| Turpinal SL | 1.50 |
| Texapon NSO | 2.00 |
| DOW Corning DB 110 A | 0.07 |
| Aculyn 33A (acrylic polymer) | 12.00 |
| Hydrogen peroxide, 50% | 22.40 |
| Water | ad 100 |

Texapon® NSO  Lauryl ether sulfate, sodium salt (approx. 27.5% active substance; INCI name: Sodium Laureth Sulfate) (Cognis)
Aculyn® 33  Acrylic polymer (approx. 28% solids content in water; INCI name: Acrylates Copolymer) (Rohm & Haas)
Dow Corning® DB 110 A  nonionic silicone emulsion (INCI name: Dimethicone) (Dow Corning)

Strands of dark blond, light brown and dark brown hair (codes: Kerling 7/0, Fischbach & Miller 6923 and Kerling 2/0) weighing approx. 0.7 g had 4 times the quantity of the finished application mixture applied to them. After blonding the strands for 30 min at 32° C., they were washed with a conventional commercial shampoo and dried with a hair-dryer.

2.1.3-Evaluation of Lightening Power

Each strand of hair was measured colorimetrically before and after the bleaching operation. The dL value according to the following formula was used as a measure of lightening power—

$$dL = L_{after} - L_{before}$$

where $L_{after}$=lightness of the strands after bleaching;
$L_{before}$=lightness of the strands before bleaching Twelve determinations were carried out for each formulation and each hair type, the mean in each case being calculated from the individual values. The greater the dL value, the better is the lightening power of the particular formulation.

Lightening Power on Dark Blond Strands (Kerling 7/0)

| dL (comp. 1) | dL (comp. 2) | dL (inv. 1) | dL (inv. 2) | dL (inv. 3) |
|---|---|---|---|---|
| 10.8 | 12.6 | 12.8 | 13.6 | 13.2 |

Lightening Power on Light Brown Strands (Fischbach & Miller 6923)

| dL (comp. 1) | dL (comp. 2) | dL (inv. 1) | dL (inv. 2) | dL (inv. 3) |
|---|---|---|---|---|
| 12.1 | 12.8 | 13.6 | 14.1 | 13.8 |

Lightening Power on Dark Blond Strands (Kerling 2/0)

| dL (comp. 1) | dL (comp. 2) | dL (inv. 1) | dL (inv. 2) | dL (inv. 3) |
|---|---|---|---|---|
| 5.3 | 6.9 | 8.0 | 6.8 | 7.2 |

2.1.4-Interpretation of Results

Bleaching action of the different formulations can be estimated by comparing dL values. It is apparent that significantly higher dL values, and thus better lightening, was achieved with the combination according to the invention of hydrogen peroxide, the specific co-bleach activator and the cationic acyl pyridinium derivative, than was possible by using hydrogen peroxide alone or in combination with the acyl pyridinium derivative. By using this specific combination of three components, it was thus possible to achieve a substantial improvement relative to the existing prior art.

We claim:

1. Agent for lightening keratin fibers comprising, in a cosmetic carrier:
   (i) at least one cationic acyl pyridinium derivative according to formula (I)

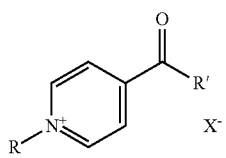

(I)

wherein
   R is a $C_1$-$C_6$ alkyl group, a $C_2$-$C_6$ alkenyl group, a $C_2$-$C_6$ hydroxyalkyl group, a $C_1$-$C_6$-alkoxy-$C_2$-$C_6$-alkyl group, a carboxy-$C_1$-$C_6$-alkyl group, an aryl-$C_1$-$C_6$-alkyl group, a heteroaryl-$C_1$-$C_6$-alkyl group, a mono- or di-$C_1$-$C_6$-alkylamino-$C_2$-$C_6$-alkyl group, a 3-oxobutyl group, a 2-oxopropyl group, an aryl group or a heteroaryl group;
   R' is a $C_1$-$C_4$ alkyl group, a $C_2$-$C_6$ hydroxyalkyl group or a $C_1$-$C_6$-alkoxy-$C_2$-$C_6$-alkyl group; and
   $X^-$ is a physiologically acceptable anion;
   (ii) at least one toxicologically safe co-bleach activator and/or the physiologically acceptable salt thereof; and
   (iii) hydrogen peroxide.

2. Agent according to claim 1, wherein R in formula (I) is a $C_1$-$C_6$ alkyl group, a $C_2$-$C_6$ alkenyl group or a $C_2$-$C_6$ hydroxyalkyl group.

3. Agent according to claim 1, wherein at least one cationic acyl pyridinium derivative according to formula (I) is chosen from 4-acetyl-1-methylpyridinium p-toluene sulfonate, 4-acetyl-1-methylpyridinium benzene sulfonate, 4-acetyl-1-methylpyridinium bromide, 4-acetyl-1-methylpyridinium hydrogen sulfate, 4-acetyl-1-allylpyridinium p-toluene sulfonate, 4-acetyl-1-allylpyridinium benzene sulfonate, 4-acetyl-1-allylpyridinium bromide, 4-acetyl-1-allylpyridinium hydrogen sulfate, 4-acetyl-1-(2-hydroxyethyl)-pyridinium p-toluene sulfonate, 4-acetyl-1-(2-hydroxyethyl)-pyridinium benzene sulfonate, 4-acetyl-1-(2-hydroxyethyl)-pyridinium bromide, or 4-acetyl-1-(2-hydroxyethyl)-pyridinium hydrogen sulfate.

4. Agent according to claim 1, wherein the at least one acyl pyridinium derivatives of formula (I) are present in an amount of 0.01 to 25 wt. %, based on total weight of the agent.

5. Agent according to claim 1, wherein the at least one co-bleach activator and/or the physiologically acceptable salt thereof is at least an aliphatic and/or carbocyclic co-bleach activator.

6. Agent according to claim 1, wherein the at least one co-bleach activator and/or the physiologically acceptable salt thereof comprises at least one functional group chosen from a hydroxy group, carboxylic acid, sulfuric acid monoester or phosphoric acid monoester.

7. Agent according to claim 1, wherein the at least one co-bleach activator is at least a co-bleach activator and/or the physiologically acceptable salt thereof according to formula (II)

(II)

wherein
   Y is a carbonyl group, a direct bond or methylene group;
   R1 is hydrogen, a $C_1$-$C_4$ alkyl group, a physiologically acceptable cation or an $SO_3^-$ or a $PO_3^{2-}$ group;
   R2 is an amino, a methylamino, a dimethylamino, a trimethylammonio group, phenyl, benzyl, phenoxymethyl, 1-naphthyl, 2-naphthyl, 2-, 3-, 4-toluoyl, or an R4-O—$(CH_2CH_2O)_n$ group, wherein R4 is a $C_6$-$C_{20}$ alkyl group and n is a number 15 or greater;
   R3 is hydrogen or an optionally branched $C_1$-$C_6$ alkyl group;
   provided that
   if Y is a carbonyl group,
     R1 is hydrogen, a $C_1$-$C_4$ alkyl group or a physiologically acceptable cation,
     R2 is an amino, a methylamino, a dimethylamino or a trimethylammonio group, and
     R3 is hydrogen or an optionally branched $C_1$-$C_6$ alkyl group,
   if Y is a direct bond,
     R1 is hydrogen,
     R2 is phenyl, benzyl, phenoxymethyl, 1-naphthyl, 2-naphthyl, 2-, 3- or 4-toluoyl, and
     R3 is hydrogen or an optionally branched $C_1$-$C_6$ alkyl group,
   or
   if Y is a methylene group,
     R1 is an $SO_3^-$ or a $PO_3^{2-}$ group,
     R2 is an R4—$O(CH_2CH_2O)_n$ group, in which R4 is a $C_6$-$C_{20}$ alkyl group and n is a number greater than 15, and
     R3 is hydrogen.

8. Agent according to claim 1, wherein the at least one co-bleach activator is at least glycine and/or the physiologically acceptable salt thereof.

9. Agent according to claim 1, wherein the at least one co-bleach activator is at least benzyl alcohol.

10. Agent according to claim 1, wherein the at least one co-bleach activator is at least a physiologically acceptable salt of R4-$O(CH_2CH_2O)_m$—$SO_3^-$, wherein R4 is a $C_6$-$C_{20}$ alkyl group and m is a number 15 or greater.

11. Agent according to claim 1, wherein the co-bleach activator and/or the physiologically acceptable salt thereof is present in an amount of 0.01 to 10 wt. %, based on total weight of the ready-to-use agent.

12. Agent according to claim 1, wherein it has a pH value of 7 to 11.

13. Agent according to claim 1 further comprising at least one inorganic persulfate or peroxodisulfate salt.

14. Method for lightening keratin fibers comprising applying an agent according to claim 1 onto keratin-containing fibers, leaving the agent on the fibers for 5 to 60 minutes, and rinsing the agent back out or washing the agent out with a shampoo.

* * * * *